United States Patent [19]

Flagg

[11] 4,250,105

[45] Feb. 10, 1981

[54] PRODUCTION OF ALIPHATIC COMPOUNDS CONTAINING ISOCYANATO AND HYDROXYL FUNCTIONALITY

[75] Inventor: Edward E. Flagg, Midland, Mich.

[73] Assignee: The Dow Chemical Company, Midland, Mich.

[21] Appl. No.: 77,871

[22] Filed: Sep. 21, 1979

Related U.S. Application Data

[63] Continuation-in-part of Ser. No. 10,299, Feb. 8, 1979, abandoned.

[51] Int. Cl.$^3$ ................ C07C 118/00; C07C 119/042
[52] U.S. Cl. ........................ 260/453 P; 260/453 AL; 544/221
[58] Field of Search ...................... 260/453 AL, 453 P

[56] References Cited

U.S. PATENT DOCUMENTS

| | | | |
|---|---|---|---|
| 3,144,468 | 8/1964 | Hoover et al. | 260/453 AL |
| 3,215,701 | 11/1965 | Pomot | 260/453 AL |
| 3,553,244 | 1/1971 | Grigat et al. | 260/453 P |
| 3,998,866 | 12/1976 | Oswald | 260/453 A |

*Primary Examiner*—Dolph H. Torrence
*Attorney, Agent, or Firm*—Douglas N. Deline

[57] ABSTRACT

Aliphatic compounds containing isocyanato and hydroxyl functionality are formed by reacting the alkali metal salt of a dihydroxy-substituted aliphatic compound with cyanogen halide producing a monomeric product containing both cyanato and hydroxyl functionality that subsequently rearranges to produce the desired compounds.

4 Claims, No Drawings

PRODUCTION OF ALIPHATIC COMPOUNDS CONTAINING ISOCYANATO AND HYDROXYL FUNCTIONALITY

CROSS-REFERENCE TO RELATED APPLICATION

This application in a continuation-in-part of U.S. patent application Ser. No. 010,299, filed Feb. 8, 1979, abandoned.

BACKGROUND OF THE INVENTION

The invention relates to aliphatic compounds containing isocyanato and hydroxyl moieties and a method of producing such compounds from corresponding hydroxy-substituted aliphatic compounds.

Only one example of an aliphatic compound containing both hydroxy and isocyanato moieties is known in the literature. Hydroxy methyl isocyanate disclosed by Hoover et al., *J. Org. Chem.*, 28, 1825 (1963) was prepared by reacting isocyanic acid with formaldehyde. The compound polymerized explosively at temperatures above 0° C. Attempts by others to produce hydroxy ethyl isocyanate and other higher molecular weight isocyanato alkanols by reacting sodium cyanate with a halo-substitued alkanol have not been successful.

SUMMARY OF THE INVENTION

The invention relates to aliphatic compounds containing isocyanato and hydroxyl moieties prepared by first reacting an alkane diol, an aliphatic diol or other aliphatic compound containing at least two hydroxy substituents with an alkali metal hydroxide or alkali metal ethoxide and subsequently reacting the alkali metal salt formed with cyanogen halide to produce compounds containing both cyanate moieties and hydroxyl moieties. The cyanate moieties of these compounds further rearrange forming isocyanate moieties. The multifunctional monomers may then undergo linear or cyclic oligomer formation.

DETAILED DESCRIPTION OF THE INVENTION

One reactant used in this process is formed from an aliphatic diol, or other multifunctional aliphatic compound having at least 2 hydroxy radicals. Such compounds are referred to herein as aliphatic polyols. Representative appropriate aliphatic polyols are compounds of the general formula HO-R-OH wherein R is an aliphatic straight or branched chain moiety of from three to twenty carbon atoms selected from the group consisting of alkyl, hydroxy-substituted alkyl and $-[CH_2(CH_2)_m X]_n-CH_2-(CH_2)_p$ wherein X is oxygen or sulfur and m, n and p are integers from one to four. Preferred are $C_{4-10}$ straight or branched chain alkylene radicals or $C_{4-10}$ remnants of polyalkylene glycols formed by the removal of both hydroxy groups.

Examples of aliphatic polyols suitable for forming the first reactant include: diethylene glycol, 1,4-butanediol, 1,6-hexane diol, glycerol, 1,2,4-butanetriol, di(2-hydroxyethyl)sulfide, triethylene glycol, tetraethylene glycol, dipropylene glycol, tripropylene glycol, 4-hydroxybutyl-2-hydroxyethyl ether, 2-hydroxyethyl-3-hydroxypropyl ether, diethylene glycol-2-hydroxyethyl ether, dipropylene glycol-2-hydroxyethyl ether, polyethylene glycol, polypropylene glycol, 2-hydroxyethyl-3-hydroxypropyl sulfide, etc.

The corresponding disodium salt of the aliphatic polyol may be prepared by treating the aliphatic polyol with sodium ethoxide or sodium hydroxide in an appropriate solvent. As a representative solvent a 40/60 volume ratio mixture of water and ethanol may be used. The process of alkoxide exchange is well-known and other appropriate solvents may be known to one skilled in the art or determined by standard techniques of chemical experimentation.

After the alkoxide exchange reaction is complete, most of the water/ethanol mixture may be removed by distillation and benzene added accompanied by additional distillation to further remove by azeotroping as much remaining water as is possible.

In the next step the resulting salt is placed in an appropriate reaction vessel containing a solvent, preferably after the salt has first been ground to a uniform consistency. Generally an aprotic organic solvent devoid of substituents that react with the salt or with cyanogen halide is a suitable solvent for use according to this step of the invention. Representative solvents for this step include diethyl ether, acetone, and acetonitrile. It is also possible to use excess cyanogen halide as the solvent. Under some conditions a low boiling alcohol may also be used. The preferred solvent is diethyl ether.

The second reactant, cyanogen halide, may then be added to the reaction vessel. It is preferred to add the cyanogen halide slowly accompanied by stirring after the reaction vessel and contents have first been cooled to a reduced temperature. The process is in general carried out in the temperature range of between −40° C. and +80° C., preferably between −40° C. and +10° C. When cyanogen chloride is used at least the initial stage of the reaction is preferably carried out at a temperature less than 13° C., the normal boiling point of cyanogen chloride. If cyanogen bromide is employed, higher temperatures may be advantageously used.

The amount of cyanogen halide used is not critical since some of the desired product is formed even for small additions of cyanogen halide. It is preferred however to add the cyanogen halide in about a stoichiometric ratio with the alkali metal alkoxide or in an excess. When cyanogen halide is chosen as the solvent for the reaction it may be present in an excess. Generally, molar ratios of cyanogen halide to alkali metal alkoxide from about 0.9 to about 30 may conveniently be used. The cyanogen halide may be employed either as a solid, liquid or gas.

By the use of the term halide is meant fluorine, chlorine, bromine, and iodine; however cyanogen chloride and cyanogen bromide are preferred second reactants, and cyanogen chloride is a most preferred second reactant.

The reaction may be conducted with a catalyst if desired. It has been found that no catalyst is required when diethyl ether or cyanogen halide is the solvent. However, improved yields were gained when using other common organic solvents such as acetone by the addition of certain known catalysts such as quaternary alkyl aminium halide or quaternary phosphonium halide salts or cyclic macromolecular ethers in small quantities.

There is no necessity to use superatmospheric pressure or subatmospheric pressure, however, the pressure may be elevated or reduced if so desired, as for instance, as an aid in dissolution of a particular reactant.

Upon addition of the cyanogen halide second reaction, sodium halide salt formation is observed and a monomeric hydroxyl-containing cyanate compound may be identified. Positive identification of such hydroxyl functionality indicates the reaction produces the desired compound having both hydroxyl and cyanate functionality. This is considered surprising in that such aliphatic compounds containing both hydroxy and cyanate functionality have not been previously reported.

The cyanate moiety of the compound formed undergoes facile isomerization particularly at slightly elevated temperatures to yield the corresponding aliphatic isocyanate compound having hydroxyl functionality. It is possible to retain both monomeric species at reduced temperatures particularly in dilute solutions of organic solvents for substantial periods of time. Preferred are temperatures of from about $-40°$ C. to about $10°$ C.

The monomeric cyanate product is of the formula NCO-R-OH and the isocyanate product has the corresponding formula OCN-R-OH where R is as previously defined. Especially preferred because of increased stability are such monomers wherein the hydroxyl and cyanate or isocyanate moieties are separated by at least four carbon atoms. Under preferred equilibrium conditions the invented compound exists primarily as the isocyanate monomer.

The compounds of the invention readily form oligomers upon prolonged retention especially at elevated temperatures. Primary products are urethanes formed by reaction of hydroxyl and isocyanate moieties from different monomers and s-triazines formed by cyclic trimerization of isocyanate moieties. Such trimers may be used as cross-linking agents and in other industrial applications.

SPECIFIC EMBODIMENTS OF THE INVENTION

Having described the invention, the following examples are included for illustrative purposes and they are not to be construed as limiting.

EXAMPLE 1

1-Isocyanato-6-Hexanol

The disodium salt of 1,6-hexane diol was prepared by an alkoxide exchange reaction with sodium ethoxide in the following manner. The diol was treated with two equivalents of sodium ethoxide in a 40/60 volume ratio mixture of water and ethanol. The water and ethanol were removed by heating and a quantity of benzene was added to further remove water by azeotroping. The product, $NaO(CH_2)_6ONa \cdot 2H_2O$ (13.1 g, 0.066 mole) had the following analysis:

|  | %C | %H |
|---|---|---|
| calculated | 36.4 | 8.1 |
| found | 33.5 | 8.3 |

The salt was removed from the reaction vessel, ground in a dry box with a mortar and pestle and placed in a liter flask equipped with a stirrer containing 400 ml of diethyl ether. After cooling the flask and contents to about $-40°$ C. in a dry ice bath an excess of cyanogen chloride, (24.4 g) was added. Precipitate formation was observed. The flask was stirred at a reduced temperature of about $-30°$ C. for about 3 or 4 hours, retained at a reduced temperature of about $-14°$ C. without concomitant stirring for approximately 16 hours and again stirred for about 9 hours at about $0°$ C. The solution was then filtered and the solvent removed by evaporation under reduced pressure.

The product was a viscous liquid. Analysis by techniques of standard chemical analysis gave results consistent with the presence of cyanate, isocyanate and hydroxyl moieties and indicated the presence of 1-cyanato-6-hexanol, 1-isocyanato-6-hexanol and oligomers thereof. The precipitate collected by filtration weighed 9.1 g and was found by x-ray diffraction analysis to consist almost entirely of sodium chloride with a minor impurity of sodium cyanate. Yield based on sodium chloride produced was approximately 96 percent.

The following is a summary of the data used to identify the above products.

| Infrared Absorption Data | | |
|---|---|---|
| approximate wavelength A | (intensity) | probable source |
| 3350 | (strong) | $-CH_2OH$ (possibly N—H) |
| 2245 | (strong) | $-OCN$ |
| 1720 | (medium strong) | $(NCO)_x$ oligomer |

| Nuclear Magnetic Resonance Data | | |
|---|---|---|
| frequency-Hertz | (ppm relative to TMS) | probable source |
| $-272$ | $(-4.53)$ | $-CH_2OCN$ |
| $-245$ | $(-4.08)$ | $(CH_2NCO)_x$ |
| $-218$ | $(-3.63)$ | 13 $CH_2OH$ |
| $-184$ | $(-3.07)$ | $-CH_2NCO$ |
| $-88$ | $(-1.47)$ | $-(CH_2)_4-$ |

| Chemical Analysis | %C | %H | %N | C:H:N |
|---|---|---|---|---|
| calculated $[OCN(CH_2)_6NCO]$ | 57.1 | 7.2 | 16.7 | 4:6:1 |
| calculated $[HO(CH_2)_6NCO]$ | 58.7 | 9.2 | 9.8 | 7:13:1 |
| found | 55.3 | 9.1 | 6.8 | ~19:37:2 |

EXAMPLE 2

Use of Acetone as Reaction Solvent

A quantity of 1,6-disodium hexanedioxide prepared in Example 1 was ground in a dry box using a mortar and pestle and added to a liter flask equipped with a stirrer containing a quantity of acetone. A small amount of $(C_2H_5)_4NI$, approximately 22 mole percent based on alkoxide salt, was added as a catalyst. The pressure was maintained at about 1 atmosphere and the flask and contents were placed in a dry ice bath and maintained at a reduced temperature of about $-30°$ C. during addition of cyanogen chloride. Precipitate formation was again observed while the reaction was continued with stirring at reduced temperature of about $-30°$ C. for about five hours. The reaction temperature was increased to about $-14°$ C. and the reaction continued for about approximately 40 hours. The temperature was increased to about $0°$ C. for about the final two hours of the reaction whereupon the reaction was discontinued and the products isolated for analysis.

A viscous liquid, brown in color was isolated. Upon analysis the existence of both isocyanate and hydroxide moieties indicating monomer presence were found.

EXAMPLE 3

Cyanogen Chloride as a Solvent

A quantity of 1,6-disodium hexanedioxide was pulverized and added to a one liter flask. Excess cyanogen chloride was added under superatmospheric pressure of approximately 5 atmospheres at a temperature of about 25° C. The reaction was continued with stirring for about 15 hours.

After completion of the reaction the products were separated by standard techniques. The solid salt cake was found to be composed predominantly of sodium chloride with cyanate moiety impurities. The viscous liquid product provided identifying data corresponding to 1-isocyanato-6-hexanol and oligomers thereof.

EXAMPLES 4-6

1-Isocyanato-4-Butanol

A quantity of 1,4-disodium butanedioxide dihydrate was prepared by a standard alkoxide exchange reaction with sodium ethoxide as in Example 1. A salt having the following analysis was obtained.

|  | %C | %H |
|---|---|---|
| calculated | 28.2 | 7.1 |
| found | 30.4 | 7.0 |

The reaction conditions of Examples 1-3 were repeated for Examples 4-6 using 1,4-disodium butanedioxide dihydrate and cyanogen chloride reactants with diethyl ether, acetone and acetonitrile, respectively, as solvents. Analysis by nuclear magnetic resonance spectroscopy and infrared spectroscopy confirmed the existence of both isocyanate and hydroxyl moieties in the product in all cases. No definitive chemical analysis or product yield determination was attempted.

EXAMPLE 7

The disodium salt of diethylene glycol was prepared as in Example 1. Upon reaction with cyanogen chloride as in Example 1 a product was obtained that was identified by infrared absorption spectroscopy and nuclear magnetic resonance spectroscopy to contain both isocyanate and hydroxyl moieties. The infrared spectrum contained a moderately strong band corresponding to —NCO and very strong band corresponding to —(NCO)$_x$ thus indicating the predominate product being the isocyanate monomer, e.g., 2-isocyanatoethyl-2-hydroxyethyl ether and the trimer.

EXAMPLE 8

The disodium salt of di(2-(hydroxyethyl)sulfide was also prepared and reacted with cyanogen chloride as in Example 1 to produce 2-isocyanatoethyl-2-hydroxyethyl sulfide. Sufficient identifying characteristics were observed of the product's infrared absorption spectrum and nuclear magnetic resonance spectrum to identify the product as containing both hydroxy and isocyanato moieties along with oligomers.

What is claimed is:

1. A process for the production of aliphatic compounds containing both isocyanato and hydroxyl functionality of the formula OCN—R—OH comprising reacting an alkali metal salt of a hydroxy-substituted aliphatic compound of the formula HO—R—OH by contacting the cyanogen halide in an organic solvent at a temperature from about −40° C. to about +80° C. wherein R is an aliphatic straight or branched chain divalent radical containing from three to twenty carbon atoms selected from the group consisting of alkylene, hydroxyalkylene, and $+CH_2(CH_2)_n—X]_n—CH_2(CH_2)_p—$ wherein X is oxygen or sulfur and m, n and p are integers from 1 to 4, respectively.

2. A process according to claim 1 wherein the organic solvent is diethyl ether, acetone or cyanogen chloride.

3. A process according to claim 1 wherein the cyanogen halide reactant is cyanogen chloride.

4. A process according to claim 1 wherein the mole ratio of cyanogen halide reactant to alkali metal salt reactant ranges from about 0.9:1 to about 30:1.

* * * * *

UNITED STATES PATENT AND TRADEMARK OFFICE
CERTIFICATE OF CORRECTION

PATENT NO. : 4,250,105

DATED : February 10, 1981

INVENTOR(S) : Edward E. Flagg

It is certified that error appears in the above-identified patent and that said Letters Patent are hereby corrected as shown below:

Column 1, line 8, "in" should read --is--.

Column 1, line 27, "halo-substitued" should read --halo-substituted--.

Column 4, line 32, third column of the table, "13 $CH_2OH$" should read -- $CH_2OH$ --.

Column 6, line 11, "di(2-(hydroxyethyl)" should read -- di(2-hydroxyethyl) --.

Column 6, line 26, "the" should read --with--.

Signed and Sealed this

Thirtieth Day of June 1981

[SEAL]

Attest:

RENE D. TEGTMEYER

Attesting Officer

Acting Commissioner of Patents and Trademarks